US009918660B2

(12) United States Patent
Zeller

(10) Patent No.: US 9,918,660 B2
(45) Date of Patent: Mar. 20, 2018

(54) METHOD FOR CORRECTING RESPIRATORY INFLUENCES ON MAGNETIC RESONANCE RECORDINGS OF AN EXAMINATION OBJECT

(71) Applicant: SIEMENS AKTIENGESELLSCHAFT, Munich (DE)

(72) Inventor: Mario Zeller, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 298 days.

(21) Appl. No.: 14/858,618

(22) Filed: Sep. 18, 2015

(65) Prior Publication Data

US 2016/0081588 A1 Mar. 24, 2016

(30) Foreign Application Priority Data

Sep. 19, 2014 (DE) .......................... 10 2014 218 901

(51) Int. Cl.
*A61B 5/08* (2006.01)
*A61B 5/055* (2006.01)
(Continued)

(52) U.S. Cl.
CPC ............ *A61B 5/0816* (2013.01); *A61B 5/055* (2013.01); *A61B 5/113* (2013.01); *A61B 5/721* (2013.01); *A61B 5/7246* (2013.01); *A61B 5/7285* (2013.01); *G01R 33/56509* (2013.01); *G06T 5/003* (2013.01); *G06T 5/50* (2013.01); *G06T 7/0012* (2013.01); *A61B 2576/00* (2013.01); *G01R 33/5673* (2013.01);
(Continued)

(58) Field of Classification Search
CPC ......... G06T 5/50; G06T 5/003; G06T 7/0012; G06T 2207/10076; G06T 2207/30004; G06T 2207/10088; A61B 2576/00; A61B 5/055; A61B 5/0816; A61B 5/721; A61B 5/7246; A61B 5/7285; A61B 5/113; G01R 33/56509; G01R 33/5673; G01R 33/5676

See application file for complete search history.

(56) References Cited

U.S. PATENT DOCUMENTS

2008/0004518 A1 1/2008 Stehning et al.
2008/0212737 A1* 9/2008 D'Souza ............... A61N 5/1049
378/65

(Continued)

OTHER PUBLICATIONS

Van De Moortele et. al., "Respiration-Induced B0 Fluctuations and Their Spatial Distribution in the Human Brain at 7 Tesla," Magnetic Resonance in Medicine, vol. 47, pp. 888-895 (2002).

(Continued)

*Primary Examiner* — Bo J Peng
(74) *Attorney, Agent, or Firm* — Schiff Hardin LLP

(57) ABSTRACT

In a method for correcting respiratory influences on recordings of an examination object by operation of a magnetic resonance apparatus, an external respiratory signal is determined, an internal respiratory signal is determined, a correlation signal is determined, at least one reliability range of the correlation signal is determined, a fit function in at least one reliability range of the correlation signal is determined, and the recordings subject to respiratory influences of the examination object are corrected based on the determined fit function.

10 Claims, 3 Drawing Sheets

(51) Int. Cl.
  *G06T 7/00* (2017.01)
  *G06T 5/00* (2006.01)
  *G06T 5/50* (2006.01)
  *A61B 5/00* (2006.01)
  *A61B 5/113* (2006.01)
  *G01R 33/565* (2006.01)
  *G01R 33/567* (2006.01)

(52) U.S. Cl.
  CPC ............ *G01R 33/5676* (2013.01); *G06T 2207/10076* (2013.01); *G06T 2207/10088* (2013.01); *G06T 2207/30004* (2013.01)

(56) References Cited

U.S. PATENT DOCUMENTS

| | | | |
|---|---|---|---|
| 2010/0121183 A1 | 5/2010 | Taguchi et al. | |
| 2011/0022375 A1 | 1/2011 | Odille et al. | |
| 2011/0152668 A1 | 6/2011 | Stemmer | |
| 2012/0004518 A1* | 1/2012 | D'Souza | A61B 5/1135 600/301 |
| 2012/0226152 A1* | 9/2012 | Porikli | A61B 5/1114 600/427 |
| 2014/0035577 A1 | 2/2014 | Blumhagen et al. | |
| 2015/0231410 A1* | 8/2015 | Khan | A61N 5/1037 600/1 |

OTHER PUBLICATIONS

Zeller et. al., "Respiration Impacts Phase Difference-Based Field Maps in Echo Planar Imaging," Magnetic Resonance in Medicine, pp. 1-6 (2013).

Xiang et. al., "Correction for Geometric Distortion and N/2 Ghosting in EPI by Phase Labeling for Additional Coordinate Encoding (PLACE)," Magnetic Resonance in Medicine, vol. 57, pp. 731-741 (2007).

Pfeuffer et. al., "Correction of Physiologically Induced Global Off-Resonance Effects in Dynamic Echo-Planar and Spiral Functional Imaging," Magnetic Resonance in Medicine, vol. 47, pp. 344-353 (2002).

* cited by examiner

METHOD FOR CORRECTING RESPIRATORY INFLUENCES ON MAGNETIC RESONANCE RECORDINGS OF AN EXAMINATION OBJECT

BACKGROUND OF THE INVENTION

Field of the Invention

The present invention concerns a method for correcting respiratory influences on recordings of an examination object acquired by operation of of a magnetic resonance apparatus, and an electronically readable data storage medium encoded with programming instructions and a magnetic resonance apparatus for implementing such a method.

Description of the Prior Art

Magnetic resonance tomography (MRT) is an imaging modality that allows the high resolution generation of sectional images of living organisms such as humans. The patient is positioned in a homogeneous magnetic field $B_0$. Gradient coils are used to modify the external magnetic field in the field of view (FOV) such that a body slice is selected and such that the generated magnetic resonance (MR) signals are spatially encoded. The acquired MR signals are entered as complex numbers into a memory that represents a mathematical domain called k-space. Each such complex number entered as a k-space data entry point has a magnitude and a phase. The subsequent reconstruction of the MR signals entered into k-space, for example using a Fourier transformation, produces an image of the selected slice that is used for the medical diagnosis. The MR signals are generated and detected using a radio-frequency system, which includes a transmit antenna that radiates radio-frequency (RF) excitation pulses into the patient, and a receive antenna, which detects the emitted RF resonance signals and forwards them for image reconstruction. The selection of a suitable pulse sequence, such as a spin echo sequence or a gradient echo sequence, and the associated sequence parameters, allow the contrast of the MR images to be varied in many ways depending on the diagnostic purpose. MRT maps body structures and is therefore a structural imaging method.

Movements during an MR recording(data acquisition), for example respiratory movements of a patient who is to be examined using MR, can result in artifacts, for example types known as ghosting, blurring and/or loss of intensity in the generated images, as well as registration errors between generated images in magnetic resonance imaging, particularly when examining the organs of the thorax and abdomen and other examination regions influenced by the respiratory movement of the patient. Such artifacts can make it difficult for a physician to make a diagnosis based on such images and can lead to lesions being overlooked.

Numerous techniques are known for reducing artifacts as a result of respiratory movement. One of these techniques is the emission of a trigger signal for acquiring magnetic resonance image data as a function of a respiratory movement, generally known as respiratory gating. Respiratory gating is a technique with which the breathing of the patient is detected during the MR measurement and assigned to the acquired measurement data. With respiratory gating the measurement data are only used for reconstruction if the detected respiratory movement associated therewith satisfies certain predeterminable criteria.

The patient's breathing can be detected using external sensors, e.g. a pneumatic cuff, or using MR signals, known as navigators. A navigator is generally a short sequence in which MR signals are acquired, for example from the diaphragm or another signal source in the examination object, the movement of which is correlated with the patient's breathing. The respiratory movement can be tracked by the position of the diaphragm or the other signal source represented by the navigator.

A phase navigator can be used to obtain a respiratory signal or a correction signal from a phase difference between two non-phase-encoded navigator signals recorded shortly after one another. Susceptibility changes produced by lung movement ultimately result in different phase differences between the respective navigators. Because the susceptibility changes still have an effect a significant distance away, a phase navigator acquisition can also take place in an imaging slice and does not have to be specially positioned.

With respiratory gating using navigators, the navigator sequence can be interleaved with the imaging sequence, and the diaphragm position measured with a navigator is then assigned to the imaging data acquired immediately after or before.

A distinction is made between retrospective and prospective respiratory gating.

With retrospective respiratory gating the respiratory movement is detected and recorded but not evaluated during the MR measurement. Rather, the data entry points in the memory representing k space are filled a number of times. Only some of the measured data is used for reconstruction, preferably the measured data for which the respiratory signal lies within a specified window around a marked respiratory position. When a specified k space data point required for image reconstruction has been measured (i.e., an MR data entry is made thereat) a number of times within the marked window, the data can be averaged. However when a data point has always been measured outside the window, the data point with the smallest deviation from the marked position can be used for reconstruction.

With prospective respiratory gating, the physiological respiratory signal measured with the use of a respiratory sensor (e.g. the diaphragm position measured using a navigator sequence) is evaluated during measurement and the MR measurement is controlled based on the detected physiological signal. In the simplest embodiment, known as the acceptance/rejection algorithm (ARA), the measurement of an imaging data packet (and in some instances the assigned navigator sequence) is repeated until the physiological signal falls within a previously defined acceptance window.

A further option for reducing artifacts is to implement the reconstruction algorithm with a movement compensation. Here the image data are segmented into states of different respiratory stages after a respiratory process has been detected. After the images for the corresponding respiratory stages have been reconstructed, a movement model is estimated by image registration and this is used in turn to reconstruct a movement-free image volume.

While signals measured using external sensors do not take into account the distance between MR slices and the lung or longer-term phase effects, signals acquired directly by an MR measurement are frequently subject to noise and phase errors and are often only reliable for a limited number of slice positions.

SUMMARY OF THE INVENTION

An object of the present invention is to provide a method that allows correction of respiratory influences by a combination of external and internal MR measurements and at the same time overcomes the disadvantages of the individual methods.

This object is achieved in accordance with the invention by a method for correcting respiratory influences on recordings of an examination object by operation of a magnetic resonance apparatus, that includes determining an external respiratory signal, determining an internal respiratory signal, determining a correlation signal, determining at least one reliability range of the correlation signal, determining a fit function in at least one reliability range of the correlation signal, and correcting the recordings subject to respiratory influences of the examination object based on the determined fit function.

An external respiratory signal as used herein is a respiratory signal that is recorded extracorporeally, for example (but not exclusively) by a pneumatic cuff, a field camera, measurement of an RF surface reflection or a radar system, in other words by an apparatus that does not serve primarily to create a magnetic resonance image. A determination thereof as used herein means either the direct measurement of such an external respiratory signal or the downloading of an external respiratory signal from an available database if the external respiratory signal has already been recorded in advance.

An internal respiratory signal as used herein is a respiratory signal recorded by MR signals, known as navigators, in other words directly with the operation of the magnetic resonance apparatus. A determination thereof as used herein means either the direct measurement of such an internal respiratory signal or the downloading of an internal respiratory signal from an available database if the internal respiratory signal has already been recorded in advance.

A correlation signal as used herein means a signal that relates the external respiratory signal to the internal respiratory signal. The correlation signal is generally a function of the slice measured using the magnetic resonance device. The correlation signal is determined after the external respiratory signal and the internal respiratory signal have been measured, or downloaded from an available database. One example of an advantageous correlation signal in accordance with the invention is the quotient between the internal and external respiratory signals.

A determination of at least one reliability range of the correlation signal as used herein means the determination of a range that is less subject to noise and/or phase errors than, for example, a randomly selected range.

A fit function as used herein means a function that approximates closely the previously determined correlation signal. The fit function can generally be arbitrary but it can also obey a well-defined model function.

The recordings subject to respiratory influences of the examination object are then corrected based on the fit function thus corrected. In other words the respiratory artifacts produced by the respiratory influences are resolved.

Such an inventive combination of external and internal respiratory signals, in conjunction with appropriate scaling by the correlation signal and smoothing by a fit function, allows a combination of the advantages of the properties of both respiratory signals while at the same time overcoming the respective disadvantages thereof. This further optimizes the resulting image quality of a reconstruction of a magnetic resonance recording based thereon.

In an embodiment, determining the at least one reliability range takes place in a preliminary examination. A preliminary examination means an examination implemented with controlled respiratory conditions, or an evaluation of examinations already performed, in which the phase of at least one image voxel or a navigator phase, is calculated, for example slice-by-slice. Slice positions with a standard deviation that is smaller than a predetermined threshold value can then be defined as particularly reliable and can be used to determine the reliability range. This approach increases the accuracy of the method and therefore also the corresponding image quality of a magnetic resonance image based on the acquired MR data that are manipulated as described above.

In a further embodiment, determining the fit function in at least one reliability range of the correlation signal is done by averaging at least two sets of fit parameters for at least two different time points. Increasing the accuracy of the fit parameters increases the accuracy of the method and therefore also the corresponding image quality of a reconstruction of a magnetic resonance recording based thereon.

In a preferred embodiment, the determining of the fit function in at least one reliability range of the correlation signal, averaging of slice positions is implemented for at least two different time points. Increasing the accuracy of the slice positions increases the accuracy of the method and therefore also the corresponding image quality of a reconstructed magnetic resonance image.

In another embodiment, determining of the fit function in at least one reliability range of the correlation signal is done by a dynamic adjustment of fit parameters. A dynamic adjustment means an adjustment after each individual measurement. Increasing the accuracy of the fit parameters increases the accuracy of the method and therefore also the corresponding image quality of the reconstructed magnetic resonance image.

In a further embodiment, outliers of the external respiratory signal and/or of the internal respiratory signal and/or of the correlation signal are resolved. An outlier refers, for example, to an incorrectly measured point and resolving refers, for example, to the removal of the outliers and/or an interpolation with surrounding points and/or a different averaging with surrounding points and/or a different smoothing. This also increases the accuracy of the method and therefore also the corresponding image quality of the reconstructed magnetic resonance image.

In another embodiment, after the fit function has been determined in at least one reliability range of the correlation signal, the fit function is extended to at least one range that does not correspond to the aforementioned at least one determined reliability range of the correlation signal. An extension as used herein means an extrapolation of the fit function of the at least one reliability range to at least one range that does not correspond to the at least one determined reliability range of the correlation signal. This also allows the fit function to be extended to the full signal range under consideration.

In another embodiment, the recordings subject to respiratory influences of the examination object are corrected based on the extended fit function. This can increase the accuracy of the method and therefore also the corresponding image quality of the reconstructed magnetic resonance image.

The present invention also encompasses a magnetic resonance apparatus for correcting respiratory influences on recordings of an examination object.

The magnetic resonance apparatus has a magnetic resonance scanner and an external respiratory signal detector that detects an external respiratory signal as described above. The apparatus also has a control computer that operates the scanner to acquire determining an internal respiratory signal as described above. The control computer is configured to determine a correlation signal as described above, and to determine at least one reliability range of the correlation signal. The control computer is configured to determine a fit function in at least one reliability range of the correlation signal. The apparatus also has an image reconstruction computer configured to reconstruct images from MR data that are subject to respiratory influences, acquired from the examination object by the scanner, with the reconstructed images being corrected based on the determined fit function.

The present invention also encompasses a non-transitory, computer-readable data storage medium that can be loaded in a memory of a programmable controller or a computer of a magnetic resonance apparatus. The storage medium is encoded with programming instructions that cause all or various previously described embodiments of the inventive method to be implemented when the programming instructions are executed in the controller or control computer of the magnetic resonance apparatus. The programming instructions may require program means, e.g. libraries and auxiliary functions, to implement the corresponding embodiments of the method. The programming instructions can be a source code that has still to be compiled and linked or only has to be interpreted, or an executable software code that only has to be loaded into the corresponding computer for execution.

The electronically readable storage medium can be, for example, a DVD, a magnetic tape or a USB stick, on which electronically readable control information, in particular software, is stored.

The advantages of the inventive magnetic resonance apparatus and the inventive electronically readable storage medium correspond essentially to the advantages of the inventive method described in detail above. Features, advantages or alternative embodiments mentioned in the context of the method apply to the other aspects of the invention. The functional features of the method are formed by corresponding physical modules, in particular by hardware modules.

DESCRIPTION OF THE PREFERRED EMBODIMENTS

Figure 1:
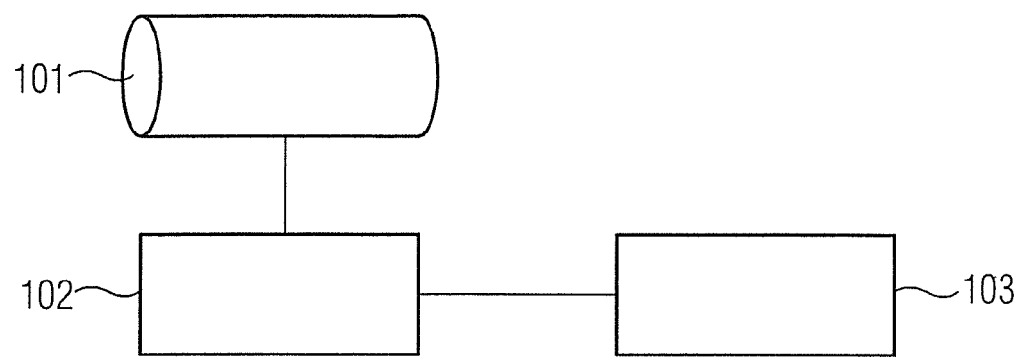
FIG. 1 schematically illustrates an inventive magnetic resonance apparatus.

FIG. 1 shows an inventive magnetic resonance device 101. The magnetic resonance device 101 has a correction computer 102 and a processing computer 103 and is configured to perform the correction of respiratory influences on recordings of an examination object.

The magnetic resonance device 101 is embodied here as a simple magnetic resonance device 101 that has a scanner and a control computer that embodies the correction computer 102 and the processing computer 103. The magnetic resonance device 101 can alternatively also comprise a combined magnetic resonance/positron emission tomography device.

Figure 2:
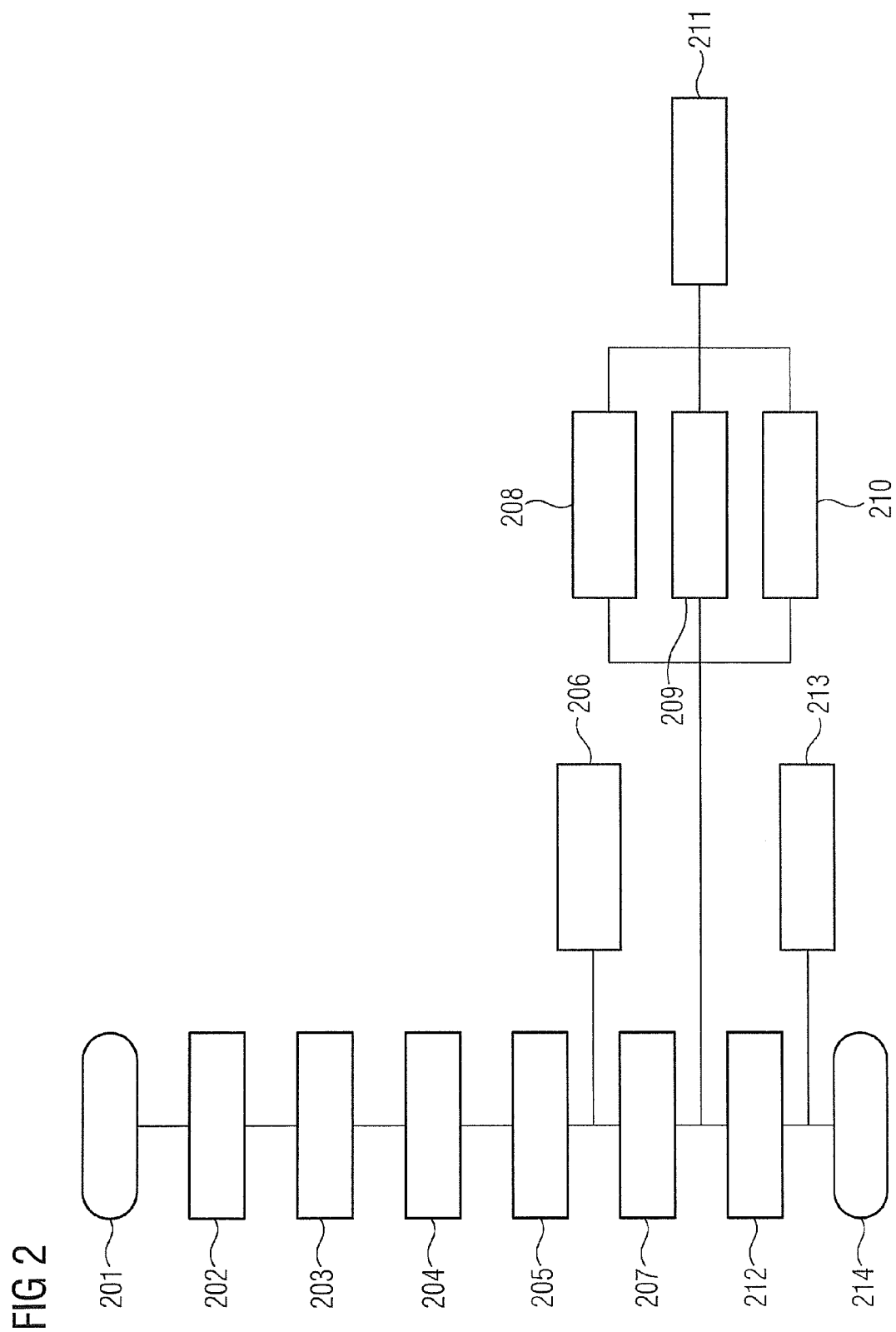
FIG. 2 is a flowchart of the inventive method.

FIG. 2 is a flowchart of an inventive method. The method comprises the method steps 201 to 214, parts of the description including the corresponding reference characters introduced in conjunction with FIG. 1 also being used in the description of method steps 201 to 214.

In a first method step 201, a method for correcting respiratory influences on recordings of an examination object by operation of the magnetic resonance device 101 is started.

In method step 202, an external respiratory signal is determined. An external respiratory signal here refers to a respiratory signal which is recorded, for example, by a pneumatic cuff, in other words by a separate device. A determination refers to either the direct measurement of said external respiratory signal or the downloading of an external respiratory signal from an available database if the external respiratory signal has already been recorded beforehand.

In method step 203, an internal respiratory signal is determined. An internal respiratory signal refers to a respiratory signal that is recorded by MR signals, known as navigators, in other words directly with the use of the magnetic resonance device 101. A determination refers to either the direct measurement of the internal respiratory signal or the downloading of an internal respiratory signal from an available database if the internal respiratory signal has already been recorded beforehand.

In method step 204, a correlation signal is determined. A correlation signal also generally refers to a signal that relates the external respiratory signal to the internal respiratory signal. The correlation signal is generally a function of the slice measured using the magnetic resonance device. The correlation signal is determined after the external respiratory signal and the internal respiratory signal have been measured, or downloaded from an available database. An example of an inventive advantageous correlation signal is the quotient between the internal and external respiratory signals.

In a method step 205, at least one reliability range of the correlation signal is determined, for example, a range is determined that is less subject to noise and/or phase errors than, for example, a randomly selected range.

Method step 206 is an optional method step, wherein the determining of the at least one reliability range takes place in a preliminary examination. A preliminary examination here refers for example to an examination in controlled respiratory conditions or an evaluation of examinations already performed, in which a phase of at least one image voxel or a navigator phase is calculated for example slice by slice. Slice positions with a standard deviation which is smaller than a previously defined threshold value can then be defined as particularly reliable and can be used to determine the reliability range.

In method step 207, a fit function is determined in at least one reliability range of the correlation signal. A fit function refers to a function which approximates closely to the previously determined correlation signal. The fit function can generally be arbitrary but it can also obey a well-defined model function.

In method step 208, the determining of the fit function in at least one reliability range of the correlation signal is an averaging of at least two sets of fit parameters for at least two different time points.

In method step 209, the determining of the fit function in at least one reliability range of the correlation signal is an averaging of slice positions for at least two different time points.

In method step 210, the determining of the fit function in at least one reliability range of the correlation signal is a dynamic adjustment of fit parameters.

During an optional method step 211 after the fit function has been determined in at least one reliability range of the correlation signal, the fit function is extended to at least one range which does not correspond to the at least one determined reliability range of the correlation signal. Such an extension means an extrapolation of the fit function of the at least one reliability range to at least one range which does not correspond to the at least one determined reliability range of the correlation signal. This also allows the fit function to be extended to the full signal range under consideration.

In method step 212, a correction of the recordings subject to respiratory influences of the examination object is made based on the determined fit function. In other words the respiratory artifacts produced by the respiratory influences are resolved.

During an optional method step 213, the recordings subject to respiratory influences of the examination object are corrected based on the extended fit function.

Outliers of the external respiratory signal and/or of the internal respiratory signal and/or of the correlation signal can also optionally be resolved at any time. An outlier here refers for example to an incorrectly measured point and resolving refers for example to the removal of the outliers and/or an interpolation with surrounding points and/or a different averaging with surrounding points and/or a different smoothing.

A last method step 214 characterizes the end of the method for correcting respiratory influences on recordings of an examination object by operation of the magnetic resonance device 101.

Figure 3:
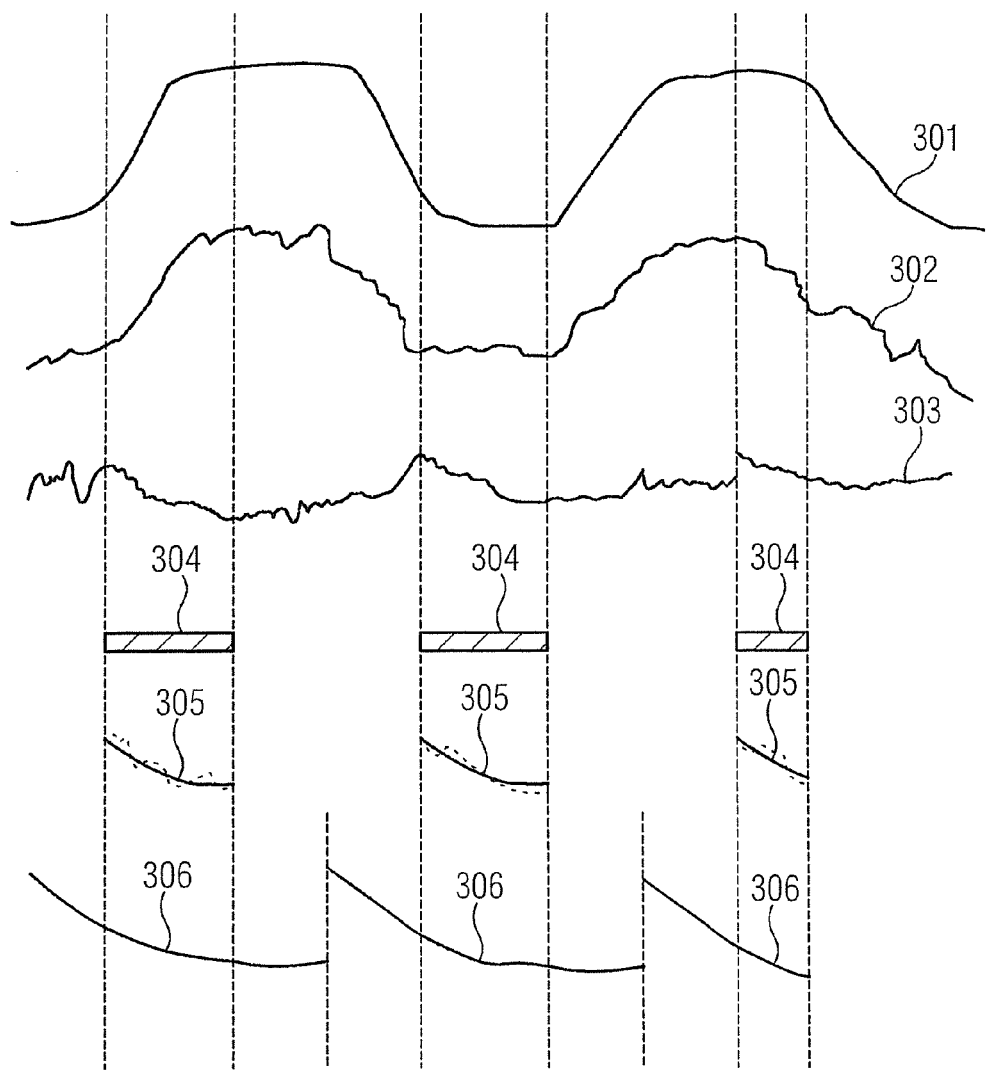
FIG. 3 shows an exemplary embodiment of the inventive method.

FIG. 3 shows an exemplary embodiment of the inventive method.

Reference character 301 indicates a determined external respiratory signal and reference character 302 a determined internal respiratory signal.

Reference character 303 indicates a determined correlation signal, in this instance the quotient between the internal and external respiratory signals, while reference character 304 indicates a number of reliability ranges of the correlation signal.

Reference character 305 in each instance indicates a fit function in the upper reliability ranges of the correlation signal and reference character 306 indicates an extension of said fit functions into other ranges.

In summary, the invention concerns a method for correcting respiratory influences on recordings of an examination object by operation of a magnetic resonance device, that includes determining an external respiratory signal, determining an internal respiratory signal, determining a correlation signal, determining at least one reliability range of the correlation signal, determining a fit function in at least one reliability range of the correlation signal, and correcting the recordings subject to respiratory influences of the examination object based on the determined fit function.

In a preferred embodiment, after the fit function has been determined in at least one reliability range of the correlation signal, the fit function is extended to at least one range which does not correspond to the at least one determined reliability range of the correlation signal and the recordings subject to respiratory influences of the examination object are corrected based on the extended fit function.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for correcting respiratory influences on magnetic resonance recordings of an examination object, comprising:
   providing a processor with a first input representing an external respiratory signal that has been acquired from a subject in a magnetic resonance scanner using a device other than the magnetic resonance scanner;
   providing said processor with a second input representing an internal respiratory signal that has been acquired from the subject using the magnetic resonance scanner;
   in said processor, determining a correlation signal that represents a relationship between said external respiratory signal and said internal respiratory signal;
   in said processor, determining at least one reliability range of said correlation signal;
   in said processor, determining a fit function in said at least one reliability range of the correlation signal; and
   in said processor, correcting magnetic resonance images, that are subject to respiratory influences, of the examination object based on said determined fit function, and making the corrected magnetic resonance images available in electronic form, as a data file, from said processor.

2. A method as claimed in claim 1 comprising determining said at least one reliability range in a preliminary examination of the examination object.

3. A method as claimed in claim 1 comprising determining said fit function in said at least one reliability range of the correlation signal by averaging at least two sets of fit parameters for at least two different time points of said correlation signal.

4. A method as claimed in claim 1 comprising determining said fit function in said at least one reliability range of the correlation signal by averaging slice positions of the examination object for at least two different time points of said correlation signal.

5. A method as claimed in claim 1 comprising determining said fit function in said at least one reliability range of said correlation signal by a dynamic adjustment of said fit parameters.

6. A method as claimed in claim 1 comprising in said processor, resolving outliers in at least one of said external respiratory signal and said internal respiratory signal and said correlation signal, before determining said fit function.

7. A method as claimed in claim 1 comprising, after determining said fit function in said at least one reliability range of said correlation signal, extending said fit function to at least one range of said correlation signal that does not correspond to said at least one determined reliability range of the correlation signal.

8. A method as claimed in claim 7 comprising correcting said magnetic resonance recordings subject to respiratory influences also based on said extended fit function.

9. A magnetic resonance apparatus comprising:
   a magnetic resonance scanner;
   a device other than the magnetic resonance scanner that detects an external respiratory signal from a subject in the magnetic resonance scanner;
   a control computer configured to operate the magnetic resonance scanner to acquire an internal respiratory signal from the subject;
   a processor configured to determine a correlation signal that represents a relationship between said external respiratory signal and said internal respiratory signal;
   said processor being configured to determine at least one reliability range of said correlation signal;

said processor being configured to determine a fit function in said at least one reliability range of the correlation signal;

said control computer being configured to acquire magnetic resonance data from the subject; and said processor being configured to reconstruct magnetic resonance images of the subject from said magnetic resonance data, and to correct magnetic resonance images that are subject to respiratory influences, based on said determined fit function, and to make the corrected magnetic resonance images available in electronic form, as a data file, from said processor.

10. A non-transitory, computer-readable data storage medium encoded with programming instructions, said storage medium being loaded into a control computer of a magnetic resonance apparatus, and said programming instructions causing said control computer to:

receive a first input representing an external respiratory signal that has been acquired from a subject in a magnetic resonance scanner using a device other than the magnetic resonance scanner;

receive a second input representing an internal respiratory signal that has been acquired using the magnetic resonance scanner;

determine a correlation signal that represents a relationship between said external respiratory signal and said internal respiratory signal;

determine at least one reliability range of said correlation signal;

determine a fit function in said at least one reliability range of the correlation signal; and correct magnetic resonance images that are subject to respiratory influences, of the examination object based on said determined fit function, and make the corrected magnetic resonance images available in electronic form, as a data file.

* * * * *